United States Patent
Watanabe et al.

(10) Patent No.: US 9,889,072 B2
(45) Date of Patent: Feb. 13, 2018

(54) POROUS SILICA PARTICLE, METHOD FOR PRODUCING THE SAME, AND CLEANSING COSMETIC CONTAINING THE SAME

(71) Applicant: JGC Catalysts and Chemicals Ltd., Kawasaki-Shi, Kanagawa (JP)

(72) Inventors: Satoshi Watanabe, Kitakyushu (JP); Naoyuki Enomoto, Kitakyushu (JP); Yasutaka Miyoshi, Kitakyushu (JP)

(73) Assignee: JGC CATALYSTS AND CHEMICALS LTD., Kawasaki-Shi, Kanagawa (JP)

( * ) Notice: Subject to any disclaimer, the term of this patent is extended or adjusted under 35 U.S.C. 154(b) by 0 days.

(21) Appl. No.: 15/512,985

(22) PCT Filed: Oct. 2, 2015

(86) PCT No.: PCT/JP2015/078043
§ 371 (c)(1),
(2) Date: Mar. 21, 2017

(87) PCT Pub. No.: WO2016/052723
PCT Pub. Date: Apr. 7, 2016

(65) Prior Publication Data
US 2017/0304161 A1  Oct. 26, 2017

(30) Foreign Application Priority Data
Oct. 2, 2014  (JP) ................. 2014-203826

(51) Int. Cl.
| | | |
|---|---|---|
| A61K 8/02 | (2006.01) | |
| A61K 8/19 | (2006.01) | |
| A61K 8/25 | (2006.01) | |
| A61K 8/34 | (2006.01) | |
| A61K 8/365 | (2006.01) | |
| A61K 8/44 | (2006.01) | |
| A61K 8/46 | (2006.01) | |
| A61K 8/60 | (2006.01) | |
| A61K 8/73 | (2006.01) | |
| A61K 8/81 | (2006.01) | |
| A61Q 19/10 | (2006.01) | |
| A61K 8/97 | (2017.01) | |
| C01B 33/12 | (2006.01) | |

(52) U.S. Cl.
CPC .............. *A61K 8/0279* (2013.01); *A61K 8/19* (2013.01); *A61K 8/25* (2013.01); *A61K 8/34* (2013.01); *A61K 8/345* (2013.01); *A61K 8/365* (2013.01); *A61K 8/44* (2013.01); *A61K 8/463* (2013.01); *A61K 8/602* (2013.01); *A61K 8/73* (2013.01); *A61K 8/8141* (2013.01); *A61K 8/97* (2013.01); *A61Q 19/10* (2013.01); *C01B 33/12* (2013.01); *A61K 2800/28* (2013.01); *A61K 2800/412* (2013.01); *A61K 2800/60* (2013.01); *C01P 2004/61* (2013.01); *C01P 2006/12* (2013.01); *C01P 2006/14* (2013.01)

(58) Field of Classification Search
None
See application file for complete search history.

(56) References Cited

U.S. PATENT DOCUMENTS

| | | | |
|---|---|---|---|
| 5,342,876 A | 8/1994 | Abe et al. | |
| 6,063,366 A | 5/2000 | Sugai et al. | |

FOREIGN PATENT DOCUMENTS

| | | | |
|---|---|---|---|
| EP | 1 627 629 A1 | 2/2006 | |
| EP | 2 228 344 A1 | 9/2010 | |
| JP | H10226621 A | 8/1998 | |
| JP | 2001278778 A | 10/2001 | |
| JP | 2010138022 A | 6/2010 | |
| JP | 2010-275260 A | 12/2010 | |
| JP | 2011225548 A | 11/2011 | |
| JP | 2013082588 A | 5/2013 | |
| WO | 2008/123284 A1 | 10/2008 | |

OTHER PUBLICATIONS

International Search Report dated Dec. 8, 2015 issued in corresponding International Application No. PCT/JP2015/078043.
Japanese Decision to Grant a Patent dated Apr. 28, 2016 issued in corresponding Japanese Patent Application No. 2016-508882.
Extended European Search Report dated Aug. 4, 2017 during the prosecution of the corresponding European Patent Application No. 15847773.7.

*Primary Examiner* — Robert A Wax
*Assistant Examiner* — William Craigo
(74) *Attorney, Agent, or Firm* — Troutman Sanders LLP

(57) ABSTRACT

A porous silica particle with the small specific surface area and large pore volume, which is contained as the scrubbing agent in the cleansing cosmetics is provided. The porous silica particle has high collapsibility, and therefore the damage of the skin can be prevented. A porous silica particle according to the present invention has: an average circularity of 0.1 to 0.5; a pore volume of $0.1 \leq Pv < 1.0$ ml/g; a specific surface area of 5 to 60 $m^2/cm^3$; a median size of 100 to 1000 μm; a ratio of a maximum particle diameter to the median size, of 3.0 or less; and a median size of 5 to 40 μm and a maximum particle diameter of 15 to 200 μm, after rubbing for 30 seconds with a load of 1.0 to 1.4 KPa.

11 Claims, 1 Drawing Sheet

POROUS SILICA PARTICLE, METHOD FOR PRODUCING THE SAME, AND CLEANSING COSMETIC CONTAINING THE SAME

CROSS-REFERENCE TO RELATED APPLICATIONS

This is a U.S. national phase application under 35 U.S.C. § 371 of International Patent Application No. PCT/JP2015/078043, filed Oct. 2, 2015, and claims benefit of priority to Japanese Patent Application No. 2014-203826, filed Oct. 2, 2014. The entire contents of these applications are hereby incorporated by reference.

TECHNICAL FIELD

The present invention relates to a porous silica particle with the small specific surface area and the large pore volume, and a method for producing the same. The present invention particularly relates to a porous silica particle that collapses when rubbed.

BACKGROUND

Cleansing cosmetics contain scrubbing agents. The scrubbing agent exfoliates the old stratum corneum by the physical action. As the scrubbing agent, microscopic plastic particles (such as polyethylene particles) have been known (See, for example, Japanese Unexamined Patent Application Publication No. 2001-278778). The plastic particles are lightweight and easily absorb chemical substances such as the pesticide and therefore, it is difficult to remove the plastic particles in the sewage treatment plant. Accordingly, the plastic particles flow into rivers, oceans, ponds, swamps, and the like, and the plastic particles are accumulated in fish and shellfish. Through such fish and shellfish, the plastic particles may have an influence on human bodies.

Japanese Unexamined Patent Application Publication No. 2011-225548 discloses that the scrubbing agent made of particular silica-gel particles provides the user with the favorable exfoliating property. At the same time, since the silica-gel particles collapse when the particles are rubbed on a subject, the stimulation on the subject is reduced.

The silica-gel particle contains water by 50 to 700%. Due to the method of producing the silica-gel particles, it is estimated that the particles have porosity. Therefore, it is concerned that the silica-gel particles might be categorized as the nanomaterial described below. It has not been verified that the particles categorized as the nanomaterial directly lead to the serious problem in environment, health, or safety but users and consumers will demand to avoid using the particles categorized as the nanomaterial.

In the announcement made by the European Commission as of Oct. 18, 2011, the substances or materials which satisfy any of the following (1) and (2) are categorized as the nanomaterial.

(1) the substances or materials containing particles for more than 50% in the number size distribution in the range of 1 to 100 nm (2) the substances or materials with a specific surface area (SA) per unit volume of more than 60 $m^2/cm^3$ (the substances or materials whose specific surface area per unit weight is more than 27 $m^2/g$ at a silica gravity of 2.2 $g/cm^3$)

The typical porous silica particles have both the nanometer-size pores and the large specific surface area and therefore correspond to the nanomaterial.

If the definition of the nanomaterial is introduced to REACH in the future, it may be possible that the submission of various kinds of documents for the use of the particles categorized as the nanomaterial is required. Therefore, the time and cost may be required in the procedure and this may interrupt the industrial use.

Japanese Unexamined Patent Application Publication No. 10-226621 discloses the cosmetic containing the collapsible particles. Here, the particle diameter is 100 to 2000 μm, the mean particle diameter of the primary particles is 100 μm or less, and the micro compression strength is 0.002 to 0.1 $kgf/mm^2$. However, since the primary particles contained in the cosmetic are large, the particles themselves have high strength. For this reason, this cosmetic tends to hurt the corneum, gives the very raspy feeling, and so on; thus, the texture characteristics required for the scrubbing agent cannot be obtained easily.

SUMMARY

An object of the present invention is to provide a collapsible porous silica particle with the small specific surface area and the large pore volume and a method for producing the same. Another object of the present invention is to provide a cleansing cosmetic containing the porous silica particle with such characteristics as a scrubbing agent.

The porous silica particle according to the present invention has the following characteristics (i) to (vi).

(i) An average circularity of 0.1 to 0.5
(ii) A pore volume (Pv) of 0.1≤Pv<1.0 ml/g
(iii) A specific surface area of 5 to 60 $m^2/cm^3$
(iv) A median size (D50) of 100 to 1000 μm
(v) A ratio of a maximum particle diameter (D100) to the median size (D50) (D100/D50), of 3.0 or less
(vi) A median size (DR50) of 5 to 40 μm and a maximum particle diameter (DR100) of 15 to 200 μm, after rubbing for 30 seconds with a load of 1.0 to 1.4 KPa.

Moreover, when a compressive force f1 of 0.5 gf is applied to the porous silica particle, a displacement of 0.5 to 3 μm occurs. Furthermore, when the compressive force that is increased up to 2.5 gf at a proportion of 0.21 gf/sec is applied to the porous silica particle, five or more displacements in a stepwise shape occur, each displacement ranging from 0.01 to 1.0 μm.

Moreover, the porous silica particle contains silica microparticles with a mean particle diameter of 100 to 1000 nm.

Moreover, a method for producing a porous silica particle according to the present invention includes: (A) a step of preparing silica sol containing silica microparticles with a solid content concentration of 25 to 50 mass %; (B) a step of dispersing a silicate solution containing silicate with a solid content concentration of 1 to 40 mass % in the silica sol to obtain slurry in which a mass ratio of a silica microparticle component to a silicate component (silica/silicate) is in the range of 90/10 to 98/2; (C) a step of drying the slurry at 100 to 400° C. for 10 minutes or less to obtain dried powder; and (D) a step of sieving the dried powder.

The porous silica particle according to the present invention has the large pore volume though the specific surface area thereof is small. When the cleansing cosmetic containing such porous silica particles as the scrubbing agent is rubbed, the particles gradually collapse and change into smaller particles. Thus, the cleansing cosmetic exhibits the mild peeling effect for the stratum corneum. In addition to that, the micro damage including the damage of the skin and the linear scar on the stratum corneum can be prevented.

DETAILED DESCRIPTION

Figure 1:
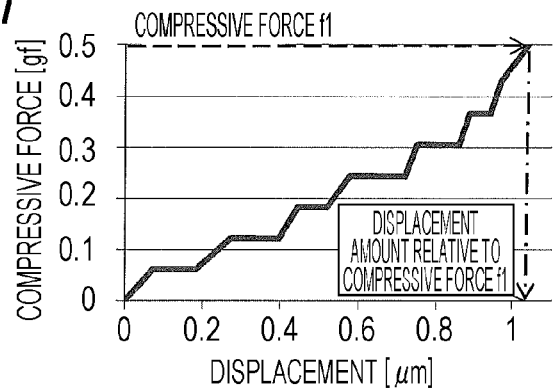
FIG. 1 is a graph expressing the relation between the compressive force and the displacement of porous silica particle according to Example 1.

Of the porous silica particles according to the present invention, the average circularity is 0.1 to 0.5, the median size (D50) is 100 to 1000 μm, and the ratio of the maximum particle diameter (D100) to the median size (D50), (D100/D50), is 3.0 or less. After the particles are rubbed for 30 seconds under a load of 1.0 to 1.4 KPa, the median size (DR50) is 5 to 40 μm and the maximum particle diameter (DR100) is 15 to 200 These values are obtained from the image data of 100 to 200 particles selected randomly from the particle group photographed with the SEM (Scanning Electron Microscope). The pore volume (Pv) of the porous silica particles obtained by the nitrogen adsorption method is 0.1 ml/g or more and less than 1.0 ml/g. The specific surface area per unit volume obtained by the BET method is 5 to 60 $m^2/cm^3$.

The porous silica particles with such characteristics can be used as the scrubbing agent for the cleansing cosmetic. When using this cleansing cosmetic, the user enjoys the exfoliating property with hard texture instantly at the start of the rubbing from the touch of the particle edge. Therefore, the user does not need to rub the cleansing cosmetic with the strong rubbing force (pressing force) to enjoy the exfoliating property. That is, the cleansing cosmetic is rubbed with the weak rubbing force naturally. Thus, the tingling feeling due to the rubbing can be suppressed and the damage of the skin and the micro damage on the stratum corneum can be prevented. Accordingly, the deterioration of the barrier function and the moisture retaining function of the stratum corneum can be prevented.

Here, when the pore volume is less than 0.1 ml/g, the porosity of the particles themselves is low. Therefore, the particle strength is high and the particles will not collapse when rubbed on the skin. In this case, the damage of the skin and the micro damage on the stratum corneum are concerned. On the other hand, when the pore volume is more than 1.0 ml/g, the porosity of the particles themselves is high. Therefore, the particle strength is low and the particles will not give the appropriate stimulation instantly when rubbed on the skin. In this case, the appropriate texture required for the scrubbing agent cannot be obtained. In addition, the particles easily collapse in the process of preparing the cosmetic. Thus, the quality of the cosmetic becomes less stable.

The porous silica particle is preferably displaced by 0.5 to 3 μm when a compressive force f1 of 0.5 gf is applied. When the compressive force that is increased up to 2.5 gf at a proportion of 0.21 gf/sec is applied to the porous silica particle, it is preferable that the five or more displacements in the stepwise shape occur and that each displacement is in the range of 0.01 to 1.0 μm. Assuming that the amount of displacement at a compressive force f2 of 2.5 gf is d2 (μm), the tilt (f2/d2) of the compression displacement is preferably in the range of 0.5 to 2.5.

In addition, the compressive force is continuously applied to the porous silica particle. The compressive force applied here is also increased at a proportion of 0.21 gf/sec. As the compressive force is increased, the stepwise displacement exceeds 10 μm. A compressive force f3 at which the displacement of 10 μm or more occurs first is preferably in the range of 5 to 40 gf.

The porous silica particle contains silica microparticles with a mean particle diameter of 100 to 1000 nm. The mean particle diameter can be obtained by the laser diffraction method. When the porous silica particle contains the silica microparticles in this size range as the primary particles, even if the porous silica particle has collapsed into primary particles as being rubbed, the primary particles do not correspond to the nanomaterial.

The porous silica particles may contain, in the range of 0.1 to 5 mass %, microparticles containing at least one of titanium dioxide, iron oxide, zinc oxide, an ultramarine pigment, a Prussian blue pigment, and an organic pigment. Within this range, the porous silica particle can contain the microparticles uniformly. Examples of the iron oxide include ferric oxide, iron hydroxide oxide, and triiron tetraoxide. The mean particle diameter of the microparticles is desirably equal to that of the silica microparticles. That is, the mean particle diameter is in the range of 100 to 1000 nm. By containing such microparticles, the colored porous silica particles can be obtained.

<Method for Producing Porous Silica Particle>

A method for producing the porous silica particle according to the present invention includes the following steps (A) to (E). In Step (A), silica sol containing silica microparticles with a solid content concentration of 25 to 50 mass % is prepared. In Step (B), into the silica sol, a silicate solution containing silicate with a solid content concentration of 1 to 40 mass % is dispersed; thus, slurry in which the mass ratio (silica/silicate) of the silica microparticle component to the silicate component ranges from 90/10 to 98/2 is prepared. In Step (C), dried powder is obtained by drying the slurry at 100 to 400° C. for 10 minutes or less. In Step (D), the dried powder is sieved. With such slurry, the silicate component in the particle becomes gel in the initial stage of the drying. Thus, the dried powder that collapses when rubbed is obtained. That is to say, the dried powder of the porous silica particles obtained by such a producing method has predetermined specific surface area, pore volume, particle diameter, and collapsibility.

For drying the slurry, rotating drying with the use of a commercial drum drier is suitable. Other examples include spray drying with the use of a spray drier, fluidized-bed drying with the use of a slurry drier, and airflow drying with the use of a jet drier.

A heat medium is set inside a rotating drum (cylinder) of the drum drier. The slurry supplied to the heated drum is evaporated and condensed. At the same time, the slurry is attached in a thin-film shape on the drum surface, so that the evaporation and drying are carried out quickly. While the drum rotates once, the dried substance is scraped off continuously by a fixed knife. In this case, the slurry is supplied at a speed of 5 to 25 liters per hour and thus, the dried powder with a predetermined characteristic can be obtained.

The drying time for the slurry is within 10 minutes, preferably within 1 minute. If the drying time is more than 10 minutes, the microparticles with a size of 100 nm or less derived from the silicate are generated and the specific surface area increases. The end of the drying cannot be expressed by numerals. However, the time from the start of the drying of the slurry to the start of the extraction of the dried powder can be regarded as the drying time.

It is preferable that the dried powder is crushed before the sieving. This can increase the yield of the porous silica particles.

In addition, the calcined powder may be generated by calcining the dried powder. The calcining can increase the compression strength of the porous silica particles. That is, the dried powder is calcined at 200 to 800° C. for 1 to 24 hours. If the calcination temperature is less than 200° C. or the calcination time is less than 1 hour, the siloxane bond between the primary particles contained in the porous silica particle is not sufficient, so that the improved compression strength is not expected. On the other hand, if the calcination temperature is more than 800° C., the pores in the particle disappear due to the sintering of the particles, so that the desired porosity cannot be maintained. In addition, the crystalline silica (such as quartz) may be generated. Therefore, the calcination temperature is not preferably more than 800° C. Even if the calcination time is more than 24 hours, the particular effect cannot be obtained and this is not economical.

The silicate may be formed by dealkalizing (for example, removing Na ions from) a silicate aqueous solution of alkali metal silicate or a silicate of an organic base with the cation exchange resin. Examples of the silicate include the silicate of the organic base, for example, the quaternary ammonium silicate and an alkali metal silicate such as sodium silicate (water glass) or potassium silicate. In particular, a silicate solution derived from water glass is preferable.

The mean particle diameter of the silica microparticles is preferably 100 to 1000 nm. The mean particle diameter of the porous silica particles can be obtained based on the particle size distribution measured by the laser diffraction method. The measurement of the particle size distribution by the laser diffraction method employs the laser diffraction particle diameter analyzer LA-950 (manufactured by HORIBA, Ltd.). Examples of the silica microparticles include silica, silica-alumina, silica-zirconia, and silica-titania. It is not necessary to change the production conditions for the porous silica particles depending on the composition of the silica microparticle. In consideration of mixing into the cosmetic, amorphous silica is preferable.

The slurry may contain organic microparticles as necessary. Examples of the organic microparticles include particles of polymer latex such as natural rubber, a styrene-butadiene copolymer, acrylate latex, and polybutadiene. The mean particle diameter of the organic microparticles is desirably equal to that of the silica microparticles. The preferable mean particle diameter of the organic microparticles is in the range of 100 to 1000 nm.

By heating the dried powder containing the organic microparticles at 400 to 1200° C. under the atmospheric pressure or reduced pressure, the organic microparticles are removed. Thus, the porous silica particles with the larger pore volume are obtained.

<Cleansing Cosmetic>

The cleansing cosmetic according to the present invention can be obtained by mixing the porous silica particles described above and various kinds of cleansing cosmetic components to be described below.

Known components may be contained as the various kinds of cleansing cosmetic components. Examples of the components that can be used include: various surfactants such as nonionic surfactants, cationic surfactants, anionic surfactants, and amphoteric surfactants; alcohols such as isostearyl alcohol, octyldodecanol, lauryl alcohol, ethanol, isopropanol, butyl alcohol, myristyl alcohol, cetanol, stearyl alcohol, and behenyl alcohol; various polymers such as gum arabic, carrageenan, agar, xanthan gum, gelatin, alginic acid, guar gum, albumin, pullulan, carboxyvinylpolymer, cellulose and derivatives thereof, polyacrylic acid amide, polyacrylic acid sodium, and polyvinyl alcohol; and a thickener, a wetting agent, a colorant, a preservative, a texture improver, a flavoring agent, a bactericide, an antiphlogistic agent, an extender pigment, an ultraviolet-ray absorber, and the like.

In addition, the cosmetic components described in, for example, Japanese Standards of Quasi-drug Ingredients 2006 (issued by YAKUJI NIPPO LIMITED. on June 16, Heisei 18) and International Cosmetic Ingredient Dictionary and Handbook (issued by the Cosmetic, Toiletry, and Fragrance Association, Fourteenth Edition 2014) can be used.

The cleansing cosmetic according to the present invention can be produced by the known method. The high-level mixing technique is not necessarily employed.

The cleansing cosmetic obtained in this manner is in the form of paste, liquid, gel, or the like. Specific examples include the cleansing cosmetics for body, the cleansing cosmetics for foot, and the cleansing cosmetics for face.

EXAMPLES

Specific examples of the present invention will be described below but the examples will not limit the present invention.

Example 1

Silica sol with a silica concentration of 40 mass % is prepared by 10 kg by condensing 20 kg of commercial silica sol (manufactured by JGC Catalysts and Chemicals Ltd.: SS-160 with a mean particle diameter of 160 nm and a silica concentration of 20 mass %) with a rotary evaporator. To this silica sol, 726 g of water glass (with a silica concentration of 29 mass %) according to JIS3 is added as the silicate solution. Moreover, a cation resin (SK-1B manufactured by Mitsubishi Chemical Corporation, this applies to the description below) is added thereto at one time so that the pH is adjusted to be 2.5; then, the cation resin is separated. This provides slurry having a silica microparticle concentration of 37.3 mass %, a concentration of silicate derived from water glass of 2.0 mass %, and an all-solid content concentration of 39.3 mass %.

This slurry is supplied to the drum drier (D-0405, manufactured by KATSURAGI IND. CO., LTD.) rotating at 1.5 rpm at 150° C. with a flow rate of 10 L/hr, so that the slurry is dried. The drying time is 40 seconds. After the drying, the slurry is crushed using the juicer mixer (manufactured by Hitachi, Ltd.) for 10 seconds, and thus the dried powder is obtained. In addition, this dried powder is sieved with the 26-mesh sieve (the specification based on JIS test), and thus the dried powder containing the porous silica particles is obtained. By calcining the dried powder for 4 hours at 500° C., the calcined powder of the porous silica particles is prepared. Table 1 shows the conditions of producing the porous silica particles according to the examples.

The physical properties of the porous silica particles according to the examples obtained in this manner are measured and evaluated as below. The results are shown in Table 2.

(1) Circularity, Median Size (D50), Maximum Particle Diameter (D100), and D100/D50

A SEM (scanning electron microscope) photograph (magnification: 100) of the porous silica particle group is taken. Using the SEM image analysis software (Scandium manufactured by Olympus Corporation), the values in title are obtained from the image data of 100 to 200 randomly selected particles.

(2) Specific Surface Area

The powder of the porous silica particles taken by approximately 30 ml in a magnetic crucible (B-2 type) is dried for two hours at 105° C., and then cooled down to the room temperature in a desiccator. Next, the sample is taken by 1 g, and the specific surface area (m$^2$/g) thereof is measured based on the BET method using the full-automatic surface area measuring device (Multisorb 12, manufactured by Yuasa Ionics Inc.). The measured specific surface area is converted with a silica gravity of 2.2 g/cm$^3$, so that the specific surface area per unit mass (m$^2$/cm$^3$) is obtained.

(3) Pore Volume

The powder of the porous silica particles taken by 10 g in a crucible is dried for one hour at 105° C., and then cooled down to the room temperature in a desiccator. Then, 1 g of the sample is taken into a well-washed cell and has nitrogen adsorbed thereon, and the pore volume thereof is calculated by the following formula:

Pore volume (ml/g)=(0.001567×($V-Vc$)/$W$)

In the above formula, V represents the amount of adsorption (ml) in the standard state at a pressure of 735 mmHg, Vc represents the capacity (ml) of the cell blank at a pressure of 735 mmHg, and W represents the mass (g) of the sample. The density ratio between the nitrogen gas and the liquid nitrogen is 0.001567.

(4) Maximum Particle Diameter (DR100) and Median Size (DR50) after Rubbing

The artificial skin made of urethane elastomer (bio skin plate, product No. P001-001#20, 195×130×5 Tmm, manufactured by Beaulax) is set on the electronic balance (HF4000, manufactured by A&D Engineering). At a central part of the artificial skin, the slurry formed by adding 3.8 g of pure water to 0.2 g of powder of the porous silica particles is dropped.

Subsequently, the slurry is rubbed on the skin with four fingers for 30 seconds in the arc-like shape with a load of 1.0 to 1.4 KPa. The slurry is extracted from the central part of the artificial skin and then photographed with the SEM (scanning electron microscope) (magnification: 100). From the image data of 100 to 200 particles that are randomly selected, the maximum particle diameter (DR100) and the median size (DR50) are measured using the aforementioned SEM image analysis software.

(5) Compression Displacement

Figure 2:
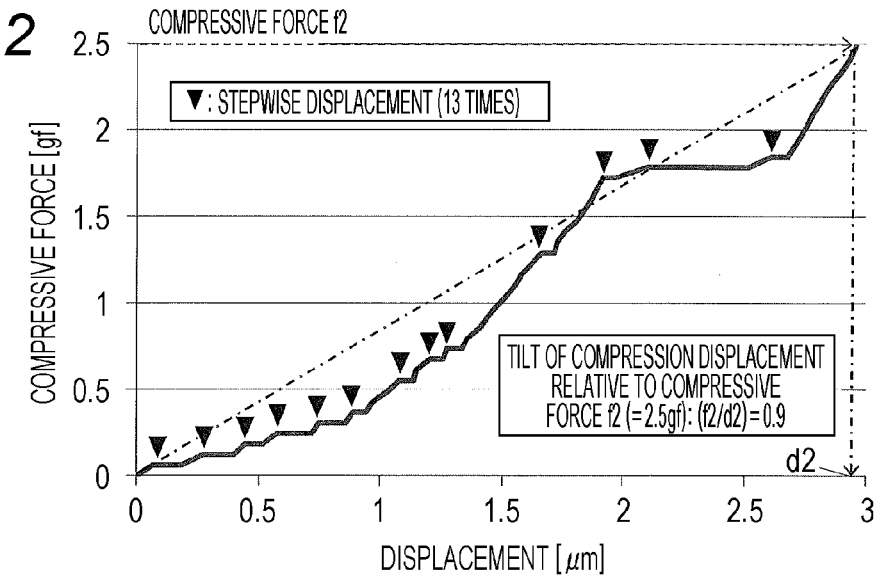
FIG. 2 is a graph expressing the relation between the compressive force and the displacement of the porous silica particle according to Example 1.
Figure 3:
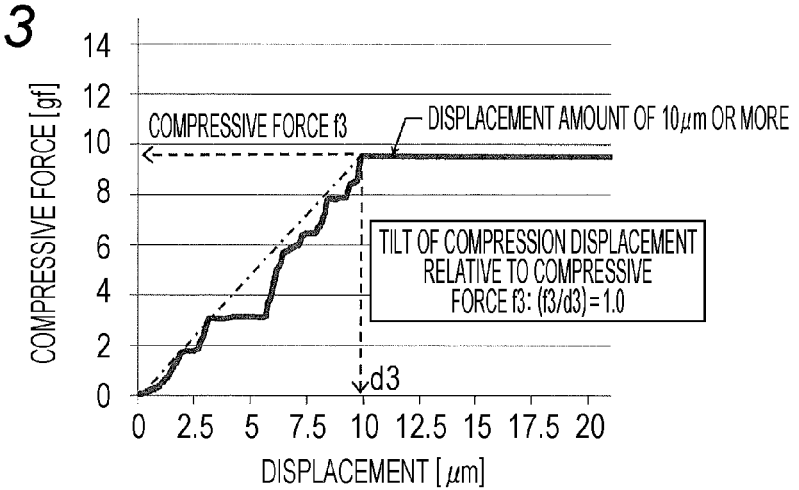
FIG. 3 is a graph expressing the relation between the compressive force and the displacement of the porous silica particle according to Example 1.

The compression displacement that occurs when the compressive force is applied to the porous silica particles is measured using the micro compression tester (MCT-210, manufactured by Shimadzu Corporation). As the indenter, "FLAT 200" (manufactured by Shimadzu Corporation) is used. FIG. 1 to FIG. 3 show the measurement results. FIG. 1 is a graph representing the displacements of the porous silica particle when a compressive force from 0 to 0.5 gf is applied at a compression speed of 0.21 gf/sec. The amount of displacement at a compressive force of 0.5 gf (compressive force f1) is obtained. In this example, the amount of displacement is approximately 1.0 µm.

FIG. 2 is a graph expressing the displacements of the porous silica particle when the applied compressive force is increased from 0 to 2.5 gf at a compression speed of 0.21 gf/sec. At this time, a plurality of displacements in the stepwise shape occurs. The stepwise displacements occur at the places on the graph where the displacement increases although the compressive force remains the same. In the graph, each start point of the stepwise displacement is drawn by an inverted triangle. In the present Example, 13 displacements in the stepwise shape are observed. At this time, each displacement amount is 0.01 to 1.0 µm. The tilt (f2/d2) of the compression displacement is calculated by obtaining the displacement d2 (µm) at a compressive force of 2.5 gf (compressive force f2). In the present example, this tilt is 0.9.

FIG. 3 is a graph expressing the displacements of the porous silica particle when the compressive force is applied until the stepwise displacement exceeds 10 µm. In this drawing, f3 denotes the compressive force when the stepwise displacement exceeds 10 µm. Here, the compressive force is applied at a compression speed of 0.21 gf/sec. By obtaining the displacement d3 (µm) at the compressive force f3, the tilt (f3/d3) of the compression displacement is calculated. Here, the displacement d3 represents the displacement measured when the stepwise displacement of 10 µm or more starts. In the present Example, the tilt of the compression displacement is 1.0. The tilt (f3/d3) of the compression displacement is preferably in the range of 0.3 to 1.25.

(6) How User Feels when Using Cleansing Cosmetic

In regard to the cleansing cosmetics containing the powder of the porous silica particles, twenty panelists conducted the sensory test. The following four items were examined by hearing from the twenty panelists: the exfoliating property, no tingling feeling, the luster of the cleansed skin, and no dullness of the cleansed skin. The results were evaluated based on the following criteria (a). Moreover, the points given by the panelists were totaled and how the panelists felt when using the cleansing cosmetics was evaluated based on the following evaluation criteria (b).

Evaluation Criteria (a)
   5: Excellent
   4: Good
   3: Average
   2: Poor
   1: Very poor Evaluation Criteria (b)
   Double circular mark: 80 or more points in total
   Single circular mark: 60 or more and less than 80 points in total
   White triangular mark: 40 or more and less than 60 points in total
   Black triangular mark: 20 or more and less than 40 points in total
   Cross mark: less than 20 points in total

TABLE 1

| | | | Example 1 | Example 2 | Example 3 | Example 4 | Example 5 | Comparative Example 1 | Comparative Example 2 | Comparative Example 3 | Comparative Example 4 | Comparative Example 5 |
|---|---|---|---|---|---|---|---|---|---|---|---|---|
| Slurry component | Silica sol | Kind of raw material silica sol | A | A | B | A | A | A | A | A | A | C |
| | | Mean particle diameter of silica microparticle (nm) | 160 | 160 | 550 | 160 | 160 | 160 | 160 | 160 | 160 | 11 |
| | | Concentration of silica microparticle component (I) (mass %) | 40.0 | 40.0 | 40.0 | 40.0 | 40.0 | 40.0 | 40.0 | 40.0 | 40.0 | 40.0 |
| | Silicate solution | Kind of silicate solution | Water glass | Water glass | Water glass | Water glass | Water glass | Water glass | Water glass | — | Water glass | Water glass |
| | | Concentration of silicate component (II) (mass %) | 29.0 | 29.0 | 29.0 | 29.0 | 29.0 | 29.0 | 29.0 | — | 29.0 | 29.0 |
| | Third component (III) | Kind of third component | — | — | — | α-iron oxide | — | — | — | — | — | — |
| Slurry | | Weight mixing ratio of components (I/II/III) | 95/5/0 | 95/5/0 | 95/5/0 | 94/5/1 | 95/5/0 | 60/40/0 | 95/5/0 | 100/0/0 | 95/5/0 | 95/5/0 |
| | | Concentration of silica microparticle (mass %) | 37.3 | 37.3 | 37.3 | 36.9 | 37.3 | 20.8 | 37.3 | 37.3 | 37.3 | 37.3 |
| | | Silicate concentration (mass %) | 2.0 | 2.0 | 2.0 | 2.0 | 2.0 | 13.9 | 2.0 | 0 | 2.0 | 2.0 |
| | | Solid content concentration of third component (mass %) | — | — | — | 0.4 | — | — | — | — | — | — |
| | | Solid content concentration of slurry (mass %) | 39.3 | 39.3 | 39.3 | 39.3 | 39.3 | 34.7 | 39.3 | 37.3 | 39.3 | 39.3 |
| Drying condition | | Equipment | | | | | | Drum drier | | | | |
| | | Slurry supply quantity (liter/hr) | 10 | 10 | 10 | 10 | 10 | 10 | 10 | 10 | 10 | 10 |
| | | Temperature (°C.) | 150 | 150 | 150 | 150 | 150 | 150 | 150 | 150 | 110 | 150 |
| | | Time (min.) | 0.67 | 0.67 | 0.67 | 0.67 | 0.67 | 1.34 | 0.67 | 0.75 | 60 | 0.67 |
| | | Time (sec.) | 10 | 45 | 10 | 10 | 10 | 10 | 10 | 10 | 10 | 10 |
| Crushing and Sieving condition | | Kind of sieves (mesh) | 26 | 83 | 26 | 26 | 26 | 26 | 26 | 26 | 26 | 26 |
| Presence or absence of Calcination | | | Presence | Presence | Presence | Presence | Absence | Presence | Presence | Presence | Presence | Presence |

Note)
Raw material silica sol A: manufactured by JGC C&C. SS-160 (mean particle diameter: 160 nm)
Raw material silica sol B: manufactured by JGC C&C. SS-550 (mean particle diameter: 550 nm)
Raw material silica sol C: manufactured by JGC C&C. Cataloid SI-30 (mean particle diameter: 11 nm)

TABLE 2

|  |  |  | Example 1 | Example 2 | Example 3 | Example 4 | Example 5 | Comparative Example 1 |
|---|---|---|---|---|---|---|---|---|
| Porous silica particle | Shape | — | Crushing shape | Crushing shape | Crushing shape | Crushing shape | Crushing shape | Crushing shape |
|  | Median size ($D_{50}$) | μm | 385 | 154 | 372 | 365 | 366 | 400 |
|  | Average carcularity | — | 0.35 | 0.4 | 0.38 | 0.3 | 0.33 | 0.39 |
|  | Specific surface area | $m^2/cm^3$ | 44 | 44 | 11 | 48 | 55 | 50 |
|  | Pore volume | ml/g | 0.36 | 0.38 | 0.39 | 0.3 | 0.40 | 0.05 |
|  | SiO2 concentration | % | 99.8 | 99.7 | 99.8 | 98.8 | 99.8 | 99.8 |
|  | Maximum particle diameter/median size ($D_{100}/D_{50}$) | — | 1.7 | 1.2 | 1.6 | 1.6 | 1.6 | 1.6 |
|  | Median size after rubbing ($D_{R50}$) | μm | 19 | 8 | 10 | 18 | 12 | 120 |
|  | Maximum particle diameter after rubbing ($D_{R100}$) | μm | 140 | 50 | 90 | 120 | 125 | 632 |
|  | Displacement amount relative to compressive force f1 (0.5 gf) | μm | 1.0 | 0.9 | 1.0 | 1.0 | 1.2 | 0.2 |
|  | The number of stepwise displacements by application of compressive force up to 2.5 gf | number of times | 13 | 14 | 12 | 13 | 11 | 0 |
|  | Compressive force f3 where 10 μm or more displacement occurs | gf | 9.8 | 9.9 | 10.3 | 9.2 | 9.1 | 50.0 |
|  | f3/f1 |  | 19.6 | 19.8 | 20.6 | 18.4 | 18.2 | 100.0 |
|  | Compression displacement (f2/d2) |  | 0.9 | 1.0 | 0.8 | 1.1 | 0.7 | 0.3 |
|  | Compression displacement (f3/d3) |  | 1.0 | 1.2 | 0.9 | 1.2 | 0.8 | 0.4 |

|  |  |  | Comparative Example 2 | Comparative Example 3 | Comparative Example 4 | Comparative Example 5 |
|---|---|---|---|---|---|---|
| Porous silica particle | Shape | — | Crushing shape | Crushing shape | Crushing shape | Crushing shape |
|  | Median size ($D_{50}$) | μm | 620 | 353 | 377 | 385 |
|  | Average carcularity | — | 0.29 | 0.29 | 0.35 | 0.35 |
|  | Specific surface area | $m^2/cm^3$ | 44 | 44 | 120 | 350 |
|  | Pore volume | ml/g | 0.36 | 0.39 | 0.35 | 0.12 |
|  | SiO2 concentration | % | 99.9 | 99.7 | 99.8 | 99.8 |
|  | Maximum particle diameter/median size ($D_{100}/D_{50}$) | — | 3.3 | 1.2 | 1.7 | 1.7 |
|  | Median size after rubbing ($D_{R50}$) | μm | 25 | 3 | 9 | 30 |
|  | Maximum particle diameter after rubbing ($D_{R100}$) | μm | 150 | 90 | 120 | 211 |
|  | Displacement amount relative to compressive force f1 (0.5 gf) | μm | 0.9 | 11 | 0.8 | 0.2 |
|  | The number of stepwise displacements by application of compressive force up to 2.5 gf | number of times | 9 | 0 | 2 | 1 |
|  | Compressive force f3 where 10 μm or more displacement occurs | gf | 9.0 | 2.0 | 8.9 | 43.0 |
|  | f3/f1 |  | 18.0 | 4.0 | 17.8 | 86.0 |
|  | Compression displacement (f2/d2) |  | 1.5 | 10 | 2.0 | 0.1 |
|  | Compression displacement (f3/d3) |  | 2.0 | 11 | 3.0 | 0.3 |

Example 2

As shown in Table 1, the crushing time was set to 45 seconds. The 83-mesh sieve (the specification based on JIS test) was used. Except these, the same method as that of Example 1 was employed to prepare and evaluate the calcined powder of the porous silica particles.

Example 3

In the present Example, SS-550 (with a mean particle diameter of 550 nm and a silica concentration of 20 mass %) manufactured by JGC Catalysts and Chemicals Ltd. is used as the raw material silica sol. Except these, the same method as that of Example 1 was employed to prepare and evaluate the calcined powder.

Example 4

In the present Example, 9.9 kg of silica sol with a silica concentration of 40 mass % is used and 40 g of α-iron oxide (II) is added to the slurry as a third component. Except these, the same method as that of Example 1 was employed to prepare and evaluate the calcined powder.

Example 5

The dried powder of the porous silica particles was prepared and evaluated by the same method as that of Example 1 except that the calcining step was not carried out.

Comparative Example 1

The calcined powder was prepared and evaluated by the same method as that of Example 1 except that the mass ratio of the silica microparticle component to the silicate component in the slurry (silica/silicate) was set to 60/40. Since the silicate component is contained more, silicate enters the gap between the primary particles contained in the porous silica particles and thus secondary particles are formed. Therefore, the particle has higher strength and the pore volume becomes smaller. Thus, the porous silica particles with the desired collapsibility cannot be obtained.

Comparative Example 2

The calcined powder was prepared and evaluated by the same method as that of Example 1 except that the sieving step using the sieve was not carried out. In the present Comparative Example, many coarse particles existed because the sieving step was not carried out, and thus, the maximum particle diameter was large. In this case, even if the rubbing force is weak, the skin may be damaged at the start of the rubbing.

Comparative Example 3

Slurry was prepared by adding pure water instead of the silicate component. The mass ratio of the silica microparticle component to the silicate component in the slurry (silica/silicate) was set to 100/0. Except this, the method similar to that of Example 1 was employed to prepare and evaluate the calcined powder. Since only the silica microparticles are used, the particle failed to have high strength. As a result, the collapse occurred at the low compressive force and the scrubbing effect was not obtained.

Comparative Example 4

The calcined powder was prepared and evaluated by the same method as that of Example 1 except that the drying temperature was changed to 110° C. and the drying time was changed to 60 minutes.

Comparative Example 5

The calcined powder was prepared and evaluated by the same method as that of Example 1 except that SI-30 (with a mean particle diameter of 11 nm and a silica concentration of 20 mass %) manufactured by JGC Catalysts and Chemicals Ltd. was used as the raw material silica sol. Since the mean particle diameter of the silica microparticles is small, the specific surface area of the porous silica particle is large and the particle has higher strength. Therefore, the desired collapsibility was not obtained.

<Preparation of Cleansing Cosmetic for Body>

The porous silica microparticles obtained in Examples 1 to 5 or the calcined powder obtained in Comparative Examples 1 to 5, which correspond to the component (1), and other components (2) to (15) were put into a beaker to satisfy the mixing ratio (mass %) shown in Table 3. By stirring the component (1) and the component (2) with a homogenizer, the components were mixed uniformly.

Thus, the cleansing cosmetics for body A to E in which the porous silica microparticles according to Examples 1 to 5 were mixed, and the cosmetics a to e in which the calcined powder according to Comparative Examples 1 to 5 was mixed were obtained.

TABLE 3

| | Cosmetic components of cleansing cosmetic for body | Mixing amount (mass %) |
|---|---|---|
| (1) | Porous silica particles according to Example or Comparative Example | 5.00 |
| (2) | Water | 44.64 |
| (3) | Sodium Lauryl Sulfate | 24.00 |
| (4) | Acrylates/C10-30 Alkyl Acrylate Crosspolymer | 10.00 |
| (5) | Corn Powder Hydrozylate | 8.00 |
| (6) | Propanediol | 5.20 |
| (7) | Carrageenan | 0.80 |
| (8) | Sodium Chloride | 0.50 |
| (9) | Phenoxyethanol, Ethylhexylglycerin | 0.50 |
| (10) | Flavoring Agent | 0.50 |
| (11) | Xanthan Gum | 0.40 |
| (12) | Sodium Laurylglucosides Hydroxypropylsulfonate | 0.30 |
| (13) | Sodium Hydroxide | 0.10 |
| (14) | Lactic Acid | 0.05 |
| (15) | EDTA-2Na | 0.01 |

Next, how the user felt the cosmetics A to E and the cosmetics a to e obtained in this manner (the texture during the application and the texture after the application) was evaluated by the above test method. The results are shown in Table 4.

The results show that the user felt very well with the cosmetics A to E either in the cleansing or after the cleansing. On the other hand, it has been understood that the user did not feel well with the cosmetics a to e.

TABLE 4

| | | During cleansing | | After cleansing | | |
|---|---|---|---|---|---|---|
| | Evaluation sample | Exfoliating property | No tingling feeling | Luster of skin | No dulness of skin | No tingling feeling |
| Example | Cosmetic A | ⊚ | ⊚ | ⊚ | ○ | ○ |
| | Cosmetic B | ○ | ⊚ | ⊚ | ○ | ○ |
| | Cosmetic C | ⊚ | ⊚ | ⊚ | ⊚ | ○ |
| | Cosmetic D | ⊚ | ⊚ | ⊚ | ○ | ○ |
| | Cosmetic E | ○ | ⊚ | ○ | ○ | ○ |
| Comparative Example | Cosmetic a | ⊚ | X | X | ○ | X |
| | Cosmetic b | ⊚ | X | ○ | ○ | X |
| | Cosmetic c | X | Δ | Δ | Δ | ○ |
| | Cosmetic d | ○ | ○ | ○ | ○ | ○ |
| | Cosmetic e | ⊚ | X | ○ | Δ | X |

The invention claimed is:
1. A porous silica particle comprising:
an average circularity of 0.1 to 0.5;
a pore volume of $0.1 \leq Pv < 1.0$ ml/g;
a specific surface area of 5 to 60 m$^2$/cm$^3$;
a median size of 100 to 1000 μm;
a ratio of a maximum particle diameter to the median size, of 3.0 or less; and
a median size of 5 to 40 μm and a maximum particle diameter of 15 to 200 μm, after rubbing for 30 seconds with a load of 1.0 to 1.4 KPa.

2. The porous silica particle according to claim 1, wherein when a compressive force of 0.5 gf is applied to the porous silica particle, a displacement of 0.5 to 3 μm occurs.

3. The porous silica particle according to claim 1, wherein when the compressive force that is increased up to 2.5 gf at a proportion of 0.21 gf/sec is applied to the porous silica particle, five or more displacements in a stepwise shape occur, each displacement ranging from 0.01 to 1.0 μm.

4. The porous silica particle according to claim 3, wherein when an amount of displacement at a compressive force f2 of 2.5 gf is expressed by a displacement d2 (μm), a tilt of compression displacement (f2/d2) is in the range of 0.5 to 2.5.

5. The porous silica particle according to claim 1, wherein when the compressive force that is increased at a proportion of 0.21 gf/sec is applied to the porous silica particle, a plurality of displacements in a stepwise shape occurs and a compressive force f3 at which the displacement of 10 μm or more occurs first is in the range of 5 to 40 gf.

6. The porous silica particle according to claim 5, wherein when an amount of compression displacement before the compression displacement of 10 μm or more at the compressive force f3 (gf) occurs is expressed by a displacement d3 (μm), a tilt of compression displacement (f3/d3) is in the range of 0.3 to 1.25.

7. A cleansing cosmetic comprising the porous silica particle according to claim 1, and a cleansing cosmetic component.

8. The porous silica particle according to claim 2, wherein when the compressive force that is increased up to 2.5 gf at a proportion of 0.21 gf/sec is applied to the porous silica particle, five or more displacements in a stepwise shape occur, each displacement ranging from 0.01 to 1.0 μm.

9. The porous silica particle according to claim 2, wherein when the compressive force that is increased at a proportion of 0.21 gf/sec is applied to the porous silica particle, a plurality of displacements in a stepwise shape occurs and a compressive force at which the displacement of 10 μm or more occurs first is in the range of 5 to 40 gf.

10. The porous silica particle according to claim 3, wherein when the compressive force that is increased at a proportion of 0.21 gf/sec is applied to the porous silica particle, a plurality of displacements in a stepwise shape occurs and a compressive force at which the displacement of 10 μm or more occurs first is in the range of 5 to 40 gf.

11. The porous silica particle according to claim 4, wherein when the compressive force that is increased at a proportion of 0.21 gf/sec is applied to the porous silica particle, a plurality of displacements in a stepwise shape occurs and a compressive force at which the displacement of 10 μm or more occurs first is in the range of 5 to 40 gf.

* * * * *